United States Patent [19]

Nordqvist

[11] Patent Number: 4,944,589

[45] Date of Patent: Jul. 31, 1990

[54] METHOD OF REDUCING THE SUSCEPTIBILITY TO INTERFERENCE OF A MEASURING INSTRUMENT

[75] Inventor: Karl G. Nordqvist, Viken, Sweden

[73] Assignee: Tecator AB, Hoganas, Sweden

[21] Appl. No.: 247,689

[22] Filed: Sep. 22, 1988

[30] Foreign Application Priority Data

Dec. 8, 1987 [SE] Sweden .................................. 8704886

[51] Int. Cl.$^5$ ............................ G01J 3/18; G01J 3/51; G01N 21/27
[52] U.S. Cl. ................................ 356/326; 250/252.1; 356/328; 356/414; 356/416
[58] Field of Search ........................ 250/252.1 A, 341; 356/326, 414, 416, 328; 364/498

[56] References Cited

U.S. PATENT DOCUMENTS 4,627,008 12/1986 Rosenthal ....................... 356/416 X

OTHER PUBLICATIONS

Martens & Naes, "*Multivariate Calibration. I. Concepts and Distinctions*", Trends in Analytical Chemistry, vol. 3, No. 8, 1984, pp. 204–210.

Naes & Martens, "*Multivariate Calibration*. *II. Chemometric Methods*", Trends in Analytical Chemistry, vol. 3, No. 10, 1984, pp. 266–271.

*Primary Examiner*—Vincent P. McGraw
*Attorney, Agent, or Firm*—Browdy and Neimark

[57] ABSTRACT

A method of reducing the susceptibility to interference of the measured value from a measuring instrument. The measuring instrument is of such a type where a test object is subjected to measurements with respect to a plurality of primary test object properties. Before the actual measurement, the effect has been mapped, by a calibration procedure, which these properties have on the measured value regarding a secondary property of the test object. The calibration procedure is effected on the one hand in that measurements by means of the same or similar instruments are carried out on a sufficient number of test objects each having a known value of the secondary property, and with a sufficient variation of the other test object properties affecting the secondary property, so as to cover expected variations of said properties, and, on the other hand, in that the thus obtained measured values of the primary properties are processed mathematically in such manner that a number of calibration constants in a mathematical relationship between the primary properties and the secondary property are generated. During the calibration procedure, a variation of one or several properties of the measuring instrument, or of representations thereof in the processing of the measured values, is introduced intentionally, said variation having the same order of magnitude as or being substantially greater than expected variations, when one or several test objects are being measured, without such information being supplied to the instrument.

4 Claims, No Drawings

METHOD OF REDUCING THE SUSCEPTIBILITY TO INTERFERENCE OF A MEASURING INSTRUMENT

The present invention relates generally to the measurement of at least one variable of a test object, i.e. quantitative determination of a property of the test object, and more precisely to a method of reducing the susceptibility to interference of an instrument used for such measurement.

To be acceptable, the result of the measurement, i.e. the determined value of the variable or the measured value, must have a predetermined accuracy and reliability. Furthermore, the result must frequently be quickly available.

The last-mentioned requirement divides the properties of a test object into two categories, i.e. such properties, hereinafter called primary properties, as can be quickly determined by direct measuring techniques, and such properties, hereinafter called secondary properties, as can be quickly determined only by indirect measuring techniques. By indirect measuring is here meant that a measure of a (secondary) property of the test object is obtained by measuring one or several other properties of the test object which are primary properties and thus can be quickly determined quantitatively by direct measuring, and by combining the thus obtained measured values in a predetermined mathematical relationship so as to obtain a measured value of the first-mentioned property.

Normally, direct measurement of a plurality of primary properties is necessary, since there is usually not only one primary property which is unambiguously related to the secondary property, regardless of the other properties of the test object.

The finding of said mathematical relationship between a plurality of primary properties and a secondary property of a test object is called calibration of the measuring instrument and results in the determination of a plurality of calibration constants. For obtaining such calibration, a plurality of test objects whose secondary property is quantitatively determined by other means, must be measured in the measuring instrument with regard to the primary properties. Moreover, the test objects used for the calibration must have such a great variation of the secondary property to be determined, and also of other properties affecting the primary properties, as can be expected among the test objects which, after the calibration, are to be measured in the measuring instrument.

The measuring technique described above is previously known (see for instance "Trends in Analytical Chemistry", Vol. 3, No. 8, 1984, pp 204–210, and No. 10, 1984, pp 266–271) and can be used for e.g. determining the concentration of a substance (secondary property) in a sample (test object) by spectrophotometry, i.e. measuring the absorption of light in the sample at a plurality of different wavelengths (primary properties). The instrument used in this example is a spectrophotometer in which a monochromator, such as a lattice monochromator or filter monochromator, is included for illuminating the sample by near monochromatic radiation at an optional number of wavelengths (measuring points) within a wave range, e.g. the near infrared range, which is suitable for measuring primary properties. Such measuring technique allows the calibration to be extended to comprise several secondary properties of the test object, such that one and the same, substantially simultaneous measurement of the primary properties of the test object can result in a quantitative determination of several secondary properties.

On calibration, the mathematical relationship is determined on the basis of an algorithm which is assumed capable of representing the relationship with sufficient accuracy, for instance the so-called PLS algorithm where PLS means "partial least square". This is a linear type algorithm and thus implies a linear relationship between the primary properties and the secondary property or each of the secondary properties, respectively. However, a nonlinear relationship can be handled, for instance by using in the algorithm not the actual measured value of a primary property, but a nonlinear function of the measured value.

It should here be stressed that the mathematical relationship determined by the calibration will pay regard to the remaining properties of the test object which affect the determination of the desired secondary property, and that this requires no knowledge of which these other properties are, or which effect they have separately.

It has been found, in some applications, that the above-described technique of quantitatively and quickly determining a secondary property of a test object does not have sufficient repeatability. Repeated measurement of one and the same test object has thus resulted in far too divergent values of the secondary property. It has been established that the main reason for this is the measuring instrument itself whose measuring parameters could not be maintained sufficiently constant. In the case of the spectrophotometer, for example, the undesired effect of poor repeatability may be due to the fact that the wavelengths in the monochromator are not maintained sufficiently constant during the measurement. The repeatability can be maintained at a required high level by using a top quality monochromator, but this is extremely costly and also places high demands on the environment in which the spectrophotometer is to be used, and this in turn considerably restricts the possibilities of practically using the instrument at all.

The object of the present invention therefore is to make it possible to reduce the susceptibility to interference of the measuring method in respect of variations in instrument parameters when using the measuring technique as described or a similar technique, without substantially increasing the cost of the measuring instrument.

This object is achieved by using the inventive method of reducing the susceptibility to interference of the measured value obtained from a measuring instrument in which a test object is subjected to measurements with respect to a plurality of primary properties whose effect on the measured value concerning a secondary test object property has been mapped by a calibration procedure which is effected on the one hand in that measurements by means of the same or a similar instrument are carried out on a sufficient number of test objects each having a known value of the secondary property, and with a sufficient variation of the other test object properties affecting the secondary property, so as to cover expected variations of said properties, and, on the other hand, in that the thus obtained measured values of said primary properties are processed mathematically in such manner that a number of calibration constants in a mathematical relationship between said primary properties and said secondary property are generated, said method of reducing the susceptibility to interference according to the invention being characterised in that a variation of one or several properties of the measuring instrument, or of representations thereof in the processing of the measured values, is introduced intentionally during the calibration procedure, said variation having the same order of magnitude as or being substantially greater than expected variations, when one or several test objects are being measured, without such information being supplied to the instrument in any other way, e.g. by external means.

In the example where primary test object properties (primary measurements) are determined spectrophotometrically, variations in the wavelength information (wavelength value) for the measuring points used for the primary measurements can be introduced intentionally during the calibration procedure for one or a plurality of the test objects used for the calibration, the wavelength variations having the same order of magnitude as or being substantially greater than the wavelength variations which may be expected during the life of the instrument due to aging, temperature variations in the surroundings, exchange of components etc. The magnitude of the wavelength shift is preferably determined by experiments. The wavelength shift desired during the calibration procedure can be obtained through a physical change in the monochromator, such as a change of the lattice position relative to the angle transducer used for reading the lattice rotary angle (and, consequently, implicitly yields the wavelength information), change of the position of the slots in a lattice or prism monochromator, variation of the filter angle or vergency of radiation incident on the filter when an interference filter monochromator is used. The wavelength shift can also be effected advantageously by a corresponding variation of the constants used for calculating the wavelengths of the monochromator on the basis of the parameters which have been measured or otherwise stated and which apply to the monochromator structure at issue, e.g. the angular position of the lattice or the interference filter.

The invention has been illustrated above by means of a single practical example, i.e. for spectrophotometric determination of primary data and when, during operation of the instrument, the wavelength shift constitutes an interference which, if the steps according to the invention are not taken, considerably impairs the performance characteristics. In both spectrophotometric determinations and other techniques of determining primary data, the invention can be used for reducing the effect of variations also in other parameters.

Practical tests have shown that the interference thus intentionally introduced has implied a sharply increased insusceptibility to the much smaller variations in the measuring instrument parameter or parameters, which are normally expected during subsequent measurements of test objects of the same type as are used in the calibration procedure. The realisation of this effect is surprising and, to a certain extent, contrary to what has been predicted, especially when the mathematical relationship is of the linear type. In this case, the variations in the measuring instrument parameter imply, in fact, a multiplicative correction, while the linear mathematical relationship used should be able to cope only with the additive corrections resulting from variations in the primary tests object properties.

If use is made of a greater variation in a plurality of measuring instrument parameters during calibration, the parameters can preferably be varied separately.

The invention has made measuring instruments utilizing the measuring technique described above operative under severe service conditions, and at a moderate cost.

Furthermore, the invention can be used for transferable calibration, i.e. a calibration made for one instrument can be used for other instruments of the same type.

It should be emphasized that the invention is not restricted to the instrument exemplified above, but is generally useful for instruments applying the described technique for quantitative determination of a secondary test object property on the basis of measured primary test object properties.

I claim:

1. A method of reducing the susceptibility to interference of a measured value obtained from a measuring instrument which measured valued has at least one property which varies during measurements an thereby introduces an unknown interference of the measurement value comprising the steps of:

subjecting a test object to measurements with respect to a plurality of primary test object properties whose effect on the measured value concerning a secondary property of said test object has been mapped by a calibration procedure which is effected by;

taking measurements by means of the same or a similar instrument which measurements are carried out on a sufficient number of calibration test objects each having a known value of the secondary property, and with a sufficient variation of the other test object properties affecting the second property, so as to cover expected variations of said properties, and by processing mathematically the thus obtained measured values of said primary properties in such manner that a number of calibration constants in a mathematical relationship between said primary properties and said secondary property are generated, and intentionally introducing during the calibration procedure a variation of at least one property of the measuring instrument, or a representation thereof in the processing of measured values, said variation having the same order of magnitude as or being substantially greater than expected variations, when one or several test objects are being measured, without information on the variation in said at least one property of the measuring instrument being supplied to said instrument in any other way.

2. The method as claimed in claim 1, said instrument being a spectrophotometer with a monochromator the wavelength of which is scanned over one or several predetermined wave ranges during a measurement, wherein the wavelength scanning or a numeric representation of said wave length is, during the calibration procedure, given a shift which for one or some of all the calibration test objects has the same order of magnitude as or is substantially greater than the shifts expected for said instrument.

3. The method as claimed in claim 2, wherein, in the case where monochromation occurs by using one or several interference filters, the wavelength is shifted by varying the vergency of radiation and/or the angle of incidence when the radiation passes or is reflected against interference filters.

4. The method as claimed in claim 2, the spectrometer consisting of a grating monochromator, wherein the wavelength is shifted by changing the angular position of the grating of said monochromator or by changing correspondingly said numerical representation of the angular position when calculating the wavelength, relative to the positions or values, for the main numbers of the measurements of the calibration test objects.

* * * * *